United States Patent [19]

Bollinger et al.

[11] 4,072,499
[45] Feb. 7, 1978

[54] USE OF PYRIDYL PHTHALIMIDES AS PLANT GROWTH REGULANTS

[75] Inventors: Frederic G. Bollinger; John J. D'Amico, both of St. Louis, Mo.

[73] Assignee: Monsanto Company, St. Louis, Mo.

[21] Appl. No.: 753,394

[22] Filed: Dec. 22, 1976

[51] Int. Cl.$^2$ .............................................. A01N 9/22
[52] U.S. Cl. ............................................. 71/94; 71/76
[58] Field of Search ............................ 71/94, 96, 76; 260/295 M

[56] References Cited

U.S. PATENT DOCUMENTS

| | | | |
|---|---|---|---|
| 2,498,497 | 2/1950 | Kirchner et al. | 260/295 M |
| 2,838,438 | 6/1958 | Pyne | 260/295 M |
| 3,658,892 | 4/1972 | Martin et al. | 260/518 A |
| 3,792,996 | 2/1974 | Barron et al. | 71/115 |
| 3,987,057 | 10/1976 | Goddard | 71/96 X |
| 4,001,272 | 1/1977 | Goddard | 71/96 X |

OTHER PUBLICATIONS

Hoffmann et al., Science, (109), 1949, p. 588.
Teubner et al., Science, (74), 1955, pp. 74–75.
Cooper et al., J. Chem. Soc., 1971, pp. 3257–3260.

*Primary Examiner*—Joseph Paul Brust
*Attorney, Agent, or Firm*—Richard H. Shear; Donald W. Peterson

[57] ABSTRACT

Certain pyridyl phthalimides have been found to be effective in regulating the growth of leguminous plants.

6 Claims, No Drawings

USE OF PYRIDYL PHTHALIMIDES AS PLANT GROWTH REGULANTS

The invention relates to a method of regulating the natural growth or development of plants by means of a chemical treatment. More specifically, the invention is directed to a method whereby the natural growth or development of leguminous plants is regulated by applying to said plants a compound having the formula

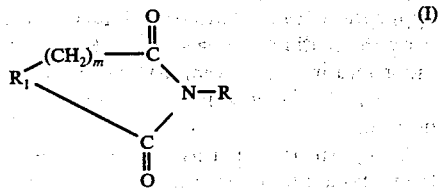

wherein R is pyridyl having one halo substituent, one lower alkyl substituent or two lower alkyl substituents; $R_1$ is selected from the group consisting of

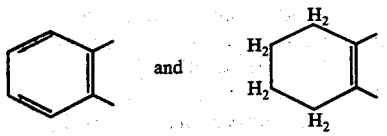

and $m$ is zero or one.

The term lower alkyl is used to include those alkyl groups having from one to four carbon atoms.

The compounds of the invention have been found to be effective plant growth regulants in spite of the fact that closely related unsubstituted pyridyl phthalimides have been found to be inactive as plant growth regulants.

As used herein, the regulation of "plant growth or development" is understood to mean the modification of the normal sequential development of a treated plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color is illustrative of higher chlorphyll activity indicative of improved rate of photosynthesis.

Although phytotoxic amounts of the active ingredient may be employed to exert a herbicidal effect, the regulation of plant growth in accordance with the present invention does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

By the term "active ingredient" is meant the active pyridyl phthalimides of formula I above. As an illustration of active ingredients useful in accordance with the present invention, the following examples are presented.

EXAMPLE 1

To a stirred solution at 120° C. containing 30 grams of phthalic anhydride in 500 ml. of xylene, 26 grams of 2-amino-5-chloropyridine was added in one portion. The stirred solution was heated at reflux for 4 to 5 hours during which time 3.6 ml. of water was removed. After stirring at 25°–30° C. for 18 hours, the slurry was cooled to 5° C., the solids collected by filtration and air dried at 25°–30° C. An 89 percent yield of N-(5-chloro-2-pyridyl)phthalimide, m.p. 153°–5° C., was obtained.

Anal. Calc'd. Cl, 13.71; N, 10.83 Found Cl, 13.87; N, 10.79.

EXAMPLE 2

A stirred slurry containing 15 grams of phthalic anhydride, 13 grams of 3-amino-2-chloropyridine, one gram of toluenesulfonic acid and 200 ml. of o-dichlorobenzene was heated at reflux for 6 hours. During this heating period 100 ml. of solvent and 1.8 ml. of water were removed. After cooling to 30° C., 50 ml. of heptane and 10 ml. of water were added and stirring was continued. The solid was collected by filtration and air dried. A 99 percent yield of N-(2-chloro-3-pyridyl) phthalimide, m.p. 156°–7° C., was obtained.

Anal. Calc'd. Cl, 13.71; N, 10.83 Found Cl, 13.54; N, 10.77.

EXAMPLE 3

Utilizing the procedure of Example 2, N-(4,6-dimethyl-2-pyridyl)phthalimide, m.p. 196°–7° C., was obtained in 99 percent yield.

Anal. Calc'd. C, 71.41; H, 4.79; N, 11.10 Found C, 71.35; H, 4.81; N, 11.07.

EXAMPLE 4

Utilizing the procedure of Example 2, N-(4-bromo-2-pyridyl)phthalimide, m.p. 162°–4° C., was obtained in 89 percent yield.

Anal. Calc'd. C, 51.51; H, 2.32; N, 9.24 Found C, 51.31; H, 2.35; N, 9.09.

EXAMPLE 5

A stirred mixture containing 0.1 mole of homophthalic anhydride, 0.1 mole of 2-amino-5-chloropyridine, one gram of p-toluenesulfonic acid and 250 ml. of o-dichlorobenzene was heated at reflux for 6 hours. During this heating period, 200 ml. of solvent and 1.8 ml. of water were removed. After cooling to 30° C., 30 ml. of water and 50 ml. of heptane were added and stirring continued. The solid was collected by filtration and air dried. A yield of 77 percent 2-(5'-chloro-2'- pyridyl)-1,3(2H,4H)-isoquinolinedione, m.p. 143°–4° C., was obtained.

Anal. Calc'd. Cl, 13.00; N, 10.27 Found Cl, 13.04; N, 10.19.

EXAMPLE 6

Utilizing a process similar to Example 5, 2-(5'-bromo-2'-pyridyl)-1,3(2H,4H)-isoquinolinedione, m.p. 288°–9° C., was obtained in 91 percent yield.

Anal. Calc'd. Br, 25.20; N, 8.83 Found Br, 25.01; N, 8.68.

EXAMPLE 7

A stirred mixture containing 15.2 g. (0.1 mole) of 3,4,5,6-tetrahydrophthalic anhydride, 0.1 mole of 2-amino-5-chloropyridine, 1 g. of p-toluenesulfonic acid and 250 ml. of o-dichlorobenzene was heated at reflux (185°–195° C.) for 6 hours. During this heating period, 180 ml. of solvent and 1.8 ml. of water were removed. The remainder of the solvent was removed in vacuo at maximum temperature of 100° C. at 1–2 mm. Upon standing at 25°–30° C. N-(5'-chloro-2'-pyridyl)-1-cyclohexene-1,2-dicarboximide, a solid melting at 106°–7° C. was obtained in 95 percent yield.

Anal. Calc'd. Cl, 13.49; N, 10.66 Found Cl, 13.29; N, 10.50.

EXAMPLE 8

Utilizing the procedure of Example 7, N(2'-chloro-3'-pyridyl)-1-cyclohexene-1,2-dicarboximide, a viscous liquid, was obtained in 95 percent yield.

Anal. Calc'd. Cl, 13.49; N, 10.66 Found Cl, 13.25; N, 10.78.

As can be seen from the above examples, the compounds of the invention may be prepared by reacting phthalic acid, homophthalic acid, or 1,2,3,4-tetrahydrophthalic acid with the appropriate aminopyridine.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given compositions readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The composition can also be applied from airplanes as a dust or spray. Should the application of the plant growth composition to the plant growth medium be desired, this is accomplished by incorporating the compositions in the soil or other media in the area where modification of the plants is desired.

Compositions of this invention generally contain from about 5 to 95 parts active ingredient, about 1 to 50 parts surface active agent and about 4 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 or more pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.01 to about 20 pounds per acre or more. The application to the soil of from 0.1 to about 10 pounds of active ingredient per acre is preferred. Foliar application to plants beginning to blossom are preferred over other types of applications.

In accordance with the present invention, certain pyridyl-phthalimides and tetrahydro analogues thereof are found to be effective growth regulators for leguminous plants, as represented by soybean (Glycine max). Significant differences between those legumes treated with the active ingredient and those not treated are found to occur. Among the differences found are a reduction in stature of the treated legume, an alteration in canopy shape and a deepening of the foliar color. Other differences include inhibition of leaf size and axillary bud development. By reducing the stature of the plant, the growing energy utilized by the plant may be directed more toward fruiting and less toward vegetation growth. This causes an increase in the plant's efficiency of production as well as an increase in the number of plants per unit area providing for an optimization of crop output. Further, shorter plants undergo less lodging. Thus, when harvested, less plants are lost and the yield is increased. Generally, plants of reduced stature tend to be more vigorous due to a greater tolerance to drought and cold.

In accordance with the practice of the invention, several plant growth regulating compositions were formulated utilizing various imides of the invention as the active ingredient. These compositions were formulated so that they could be applied in tests at a rate the equivalent of 200 gallons per acre. Table I illustrates the formulation of the composition for several application rates of active ingredient. In each formulation, the stock solution utilized is 1 percent of the active ingredient dissolved in acetone.

TABLE I

| RATE Lbs/Acre (kilos/hectare) | ml. of 1% Stock Solution | ml. Acetone | ml. 0.39% TWEEN 20 in Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |
| 0.3 (.336) | 0.1 | 1.9 | 3.6 |

Utilizing compositions formulated in accordance with Table I, several imides exhibited unexpected plant growth regulatory properties as illustrated by the test set forth in Example 9.

EXAMPLE 9

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with Table I is then applied to the pan of growing plants by overhead spray at a rate equivalent to the desired rate of active ingredient per acre. The treated pans, along with the control pans, are maintained in a greenhouse and watered from below on a sand beach and fertilized with a uniform portion of a water-soluble balanced fertilizer.

Two weeks after application of the chemical, the average height of the soybean plants in the treated pan is again measured as above and the difference in the average height before and two weeks after application represent the increase in the development of the treated pans. This development in growth of the treated plants is compared to the average increase in growth of the plants in the control pans during the same period of time. A variation of 25 percent or more in the development of at least two-thirds of the treated plants when compared to the development of the control plants demonstrates that the chemical is an effective plant regulant. Thus, a chemical is considered active when the treated plants manifest a decrease in growth of at least 25 percent less than that of the control plants, i.e., stature reduction, or an increase in growth in excess of 25 percent of that of the control plants, i.e., growth stimulation.

Table I below summarizes the results and observations made in accordance with Example 1 when the imides of the invention were utilized as the active ingredient at several rates. Some slight phytotoxicity was noted, especially at the higher application rates.

TABLE II

| Compound of Example | RATE Lbs/Acre (kilos/hectare) | Response |
|---|---|---|
| 1 | 6.0 (6.72) | Axillary bud development, leaf inhibition, slight leaf burn |
|  | 3.0 (3.36) | Axillary bud development, leaf inhibition, slight leaf burn, selective apical kill |
|  | 1.2 (1.34) | Stature reduction, axillary bud development, thick leaf texture, leaf inhibition, slight leaf burn |
|  | 0.6 (.672) | Stature reduction, axillary bud development, rosette growth, altered canopy |
| 2 | 6.0 (6.72) | Stature reduction, axillary bud development, rosette growth, leaf inhibition |
|  | 3.0 (3.36) | Stature reduction, axillary bud development, rosette growth, leaf inhibition |
|  | 1.2 (1.34) | Stature reduction, axillary bud development, rosette growth, leaf inhibition |
|  | 0.6 (.672) | Stature reduction, axillary bud development, rosette growth, leaf inhibition |
| 3 | 6.0 (6.72) | Stature reduction, axillary bud development, altered canopy |
|  | 3.0 (3.36) | Stature reduction, axillary bud development, altered canopy |
|  | 1.2 (1.34) | Axillary bud development, altered canopy |
| 4 | 6.0 (6.72) | Stature reduction, axillary bud development, leaf inhibition, rosette growth, slight leaf burn |
|  | 3.0 (3.36) | Stature reduction, axillary bud development, leaf inhibition, rosette growth, inhibition of apical development, slight leaf burn |
|  | 1.2 (1.34) | No response |
|  | 6.0 (6.72) | Axillary bud development, leaf inhibition, rosette growth, slight leaf burn |
|  | 3.0 (3.36) | Axillary bud development, leaf inhibition, rosette growth, slight leaf burn |
| 5 | 6.0 (6.72) | Stature reduction, axillary bud development, leaf alteration, altered canopy, slight leaf burn |
|  | 6.0 (6.72) | Stature reduction, axillary bud development, rosette growth, slight leaf burn |
|  | 3.0 (3.36) | Stature reduction, axillary bud development, altered canopy |
|  | 1.2 (1.34) | Stature reduction, axillary bud development, altered canopy |
| 6 | 6.0 (6.72) | Stature reduction, axillary bud development, leaf alteration, altered canopy, slight leaf burn |
|  | 3.0 (3.36) | Stature reduction, axillary bud development, leaf alteration, slight leaf burn |
|  | 1.2 (1.34) | Stature reduction, axillary bud development, altered canopy |
|  | 0.6 (.672) | Axillary bud development, altered canopy |
| 7 | 6.0 (6.72) | Axillary bud development, leaf inhibition, selective apical kill, moderate leaf burn |
|  | 3.0 (3.36) | Stature reduction, axillary bud development, selective apical kill, moderate leaf burn |
|  | 1.2 (1.34) | Stature reduction, axillary bud development, selective apical kill, moderate leaf burn |
| 8 | 6.0 (6.72) | Axillary bud development, leaf inhibition, altered canopy, slight leaf burn |
|  | 3.0 (3.36) | Stature reduction, axillary bud development, defoliation, inhibition of apical development, slight leaf burn |
|  | 1.2 (1.34) | Stature reduction, leaf distortion, slight leaf burn |
|  | 0.6 (.672) | Slight leaf burn |

Further advantages of this invention are shown in Example 10.

EXAMPLE 10

Individual soybean plants, variety Corsoy, are grown from seed in 6-inch pots containing a good grade of top soil. Two pots of 6-week old plants (5-6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15 percent in the average total height of the treated plants, when compared to the average total height of the control plants, demonstrate that the chemical is an effective plant growth regulator. Observations made utilizing the test procedure of Example 10 are summarized in Table III.

TABLE III

| Compound of Example | RATE Lbs/Acre (kilos/hectare) | Response |
|---|---|---|
| 1 | 0.126 (0.141) | Stature reduction, axillary bud development, pod set alteration |
|  | 0.063 (0.070) | Stature reduction, axillary bud development, pod set alteration |
|  | 0.25 (0.28) | Stature reduction, leaf distortion, altered canopy, pod set alteration |
|  | 0.5 (0.56) | Stature reduction, leaf distortion, altered canopy, pod set alteration, axillary bud inhibition, slight leaf burn |
| 2 | 0.5 (0.56) | Stature reduction, leaf distortion, altered canopy, axillary bud inhibition, pod set alteration |
|  | 0.25 (0.28) | Stature reduction, leaf distortion, pod set alteration |
|  | 0.1 (0.112) | Stature reduction, leaf distortion, pod set alteration |
| 3 | 5.0 (5.6) | Stature reduction, pod set alteration |
|  | 2.5 (2.80) | Stature reduction, pod set alteration |
|  | 1.0 (1.12) | No response |
| 4 | 0.25 (0.28) | Stature reduction, leaf distortion, rosette growth, thick leaf texture, pod set alteration |
|  | 0.1 (0.112) | Stature reduction, rosette growth, pod set alteration |
|  | 0.05 (0.056) | Stature reduction |
| 5 | 2.5 (2.8) | Stature reduction, chlorosis, leaf distortion, rosette growth, pod set alteration, slight leaf burn |
|  | 1.0 (1.12) | Stature reduction, leaf alteration and inhibition, pod set alteration |
|  | 0.5 (0.56) | Stature reduction, pod set alteration |
| 6 | 2.5 (2.8) | Stature reduction, chlorosis, leaf distortion |
|  | 1.0 (1.12) | Stature reduction, leaf distortion, pod set alteration |
|  | 0.5 (0.56) | Stature reduction, leaf distortion, pod set alteration |

Specifically preferred are those halo-pyridyl phthalimides having the formula

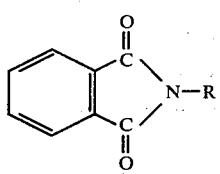

While this invention has been described with respect to certain embodiments, it is to be understood that it is not so limited and that variations and modifications thereof obvious to those skilled in the art to which this invention appertains can be made without departing from the spirit or scope thereof.

What is claimed is:

1. A method of regulating the growth of leguminous plants which comprises treating said leguminous plants with an plant growth regulating effective non-lethal amount of a compound of the formula

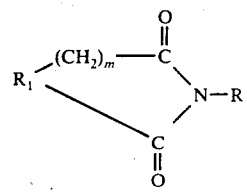

wherein R is pyridyl having one halo substituent, one lower alkyl substituent or two lower alkyl substituents; $R_1$ is selected from the group consisting of

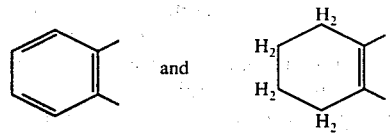

and $m$ is zero or one.

2. A method in accordance with claim 1 wherein $m$ is zero and R is pyridyl having one halo substituent.

3. A method according to claim 2 wherein said compound has the formula

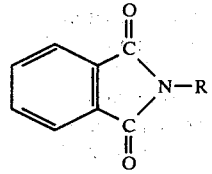

4. A composition for regulating the growth of leguminous plants which comprises from about 5 to about 95 parts of a compound having the formula

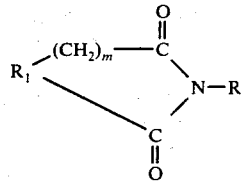

wherein R is pyridyl having one halo substituent, one lower alkyl substituent or two lower alkyl substituents; $R_1$ is selected from the group consisting of

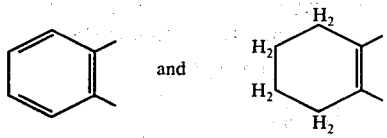

and $m$ is zero or one; the remainder parts being composed of one or more suitable carriers, diluents and/or adjuvants.

5. A composition in accordance with claim 4 wherein *m* is zero and R is pyridyl having one halo substituent.
6. A composition in accordance with claim 5 wherein said compound has the formula
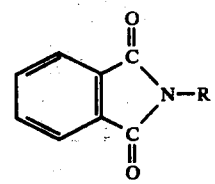
* * * * *